United States Patent
Turkington et al.

(10) Patent No.: US 6,384,416 B1
(45) Date of Patent: May 7, 2002

(54) TRANSMISSION SCANNING TECHNIQUE FOR GAMMA-CAMERA COINCIDENCE IMAGING

(75) Inventors: Timothy G. Turkington; Charles M. Laymon; R. Edward Coleman, all of Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/299,092

(22) Filed: Apr. 26, 1999

Related U.S. Application Data

(60) Provisional application No. 60/083,081, filed on Apr. 27, 1998.

(51) Int. Cl.[7] ............................................... G01T 1/166
(52) U.S. Cl. .............................. 250/363.04; 250/363.03
(58) Field of Search ....................... 250/363.04, 363.03, 250/363.1, 369

(56) References Cited

U.S. PATENT DOCUMENTS

| | | |
|---|---|---|
| 3,011,057 A | 11/1961 | Anger |
| 4,595,900 A | 6/1986 | Kamil et al. |
| 4,637,040 A | 1/1987 | Sohval et al. |
| 4,682,112 A | 7/1987 | Beer |
| 4,745,483 A | 5/1988 | Inbar |
| 5,338,936 A * | 8/1994 | Gullberg et al. ....... 250/363.04 |
| 5,486,700 A | 1/1996 | Silberklang et al. |
| 5,554,848 A | 9/1996 | Hermony et al. |
| 5,608,221 A | 3/1997 | Bertelsen et al. |
| 5,638,817 A * | 6/1997 | Morgan et al. .......... 250/363.1 |
| 5,739,540 A | 4/1998 | Motomura et al. |
| 5,900,636 A | 5/1999 | Nellemann et al. |

OTHER PUBLICATIONS

Abstract of JP 56192509, filed Nov. 30, 1981; Applicant—Shimadzu Corp,; Inventor—Seiichi Yamamoto.

* cited by examiner

Primary Examiner—Georgia Epps
Assistant Examiner—Richard Hanig
(74) Attorney, Agent, or Firm—Nixon & Vanderhye P.C.

(57) ABSTRACT

Gamma-camera coincidence (GCC) imaging systems and methods include a pair of gamma camera imaging heads rotatable about a patient-longitudinal imaging axis. The imaging heads will each have a plurality of radiation opaque septa plates extending transversely relative to the imaging axis about which they locate. Adjacent ones of the septa plates are spaced apart along said imaging axis. At least one point source of radiation will thus be positionally fixed between a predetermined adjacent pair of the septa plates of one of the imaging heads so as to be concurrently rotatable therewith.

22 Claims, 2 Drawing Sheets

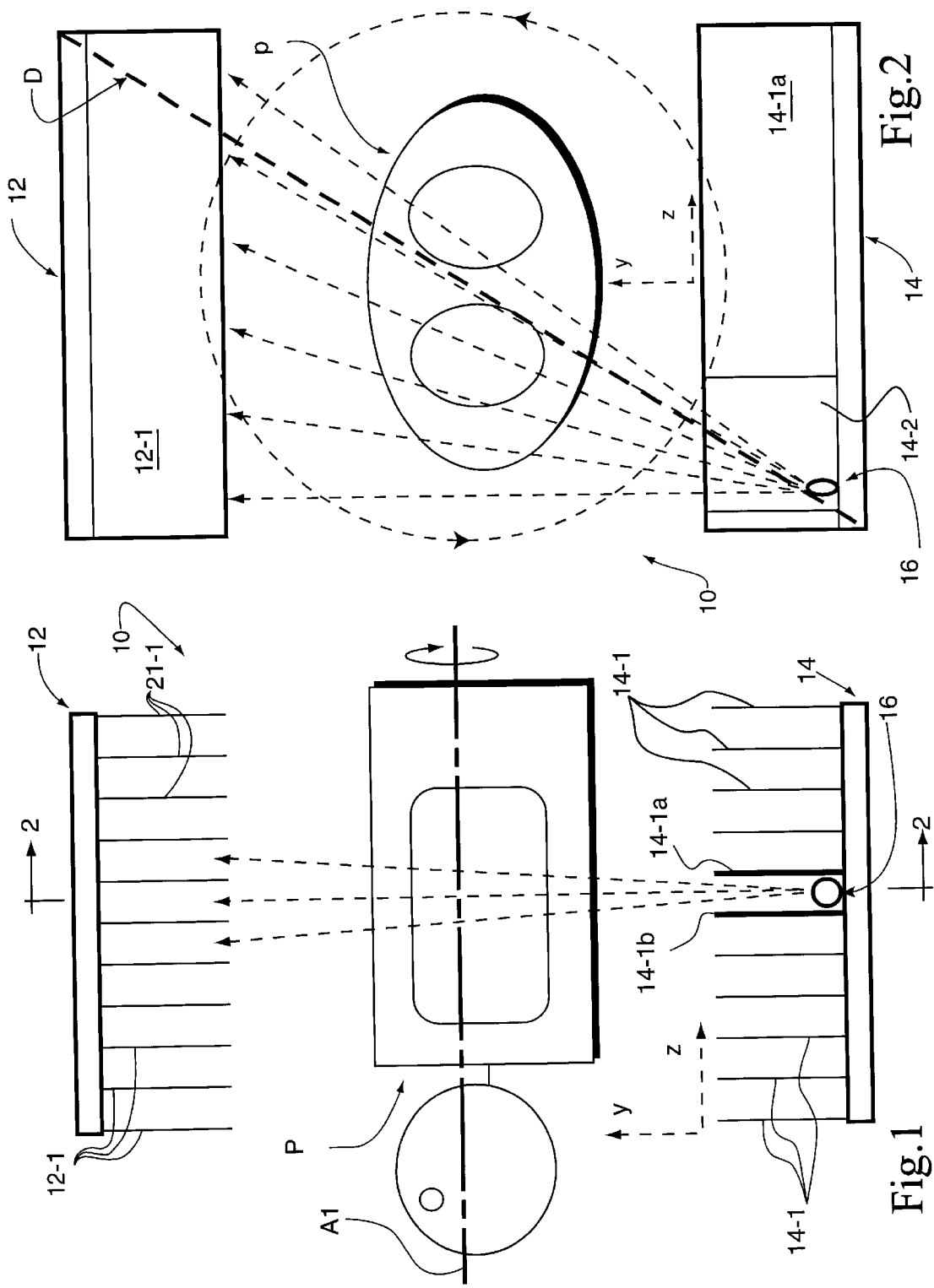

TRANSMISSION SCANNING TECHNIQUE FOR GAMMA-CAMERA COINCIDENCE IMAGING

CROSS-REFERENCE TO RELATED APPLICATION

Figure 3:
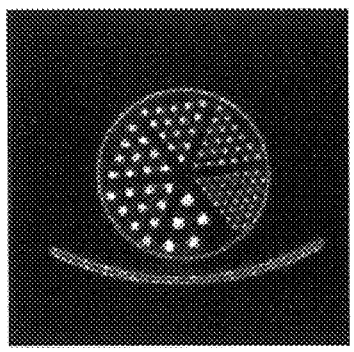

This application is related to, and claims domestic priority benefits under 35 USC §119(e) from, U.S. Provisional Patent Application Ser. No. 60/083,081 filed on Apr. 27, 1998, the entire content of which is expressly incorporated hereinto by reference.

FIELD OF THE INVENTION

The present invention relates generally to radiation imaging systems, and in particular to radiation imaging systems which are designed to perform single photon emission computed tomography (SPECT) and especially adapted to perform positron emission tomography (PET).

BACKGROUND AND SUMMARY OF THE INVENTION

Gamma (or Anger) cameras of the type disclosed in U.S. Pat. No. 3,011,057 (the entire content of which is expressly incorporated hereinto by reference), have been used extensively in nuclear medicine diagnostic imaging systems. Specifically, gamma cameras are typically employed in conjunction with a collimator to selectively filter the passage of emitted radiation of a radionuclide administered to a patient to the camera. A scintillating crystal associated with the gamma camera positioned behind the collimator emits visible light when struck by radiation. This visible light is then detected by transducers, such as photomultipliers and translated into electrical signals which can be processed in a known manner to obtain a visual image of the radionuclide distribution within the patient. In this manner, noninvasive visual imaging of a patient's organs may be obtained and used by a physician to diagnose disease.

Gamma cameras employed in conventional SPECT imaging systems, such as those described in U.S. Pat. No. 5,554,848 (the entire content of which is expressly incorporated hereinto by reference) can be modified to perform coincidence imaging (i.e., conventional positron emission tomography (PET)) by removal of the collimators and addition of electronics to detect and record simultaneous events in both cameras.

While radiation point and line sources have been employed in the past in PET imaging systems to improve image quality (e.g., see U.S. Pat. No. 4,637,040, the entire content of which is expressly incorporated hereinto by reference), such conventional point and line source techniques do not operate well when employed in conjunction with gamma cameras associated with SPECT imaging systems when used in a coincidence imaging mode.

What has been needed, therefore is a transmission scanning technique which enhances the image quality of radiation imaging systems, and particularly single photon emission computer tomography systems operating in a coincidence imaging mode. It is toward fulfilling such a need that the present invention is directed.

Broadly, the present invention is embodied in systems and methods which allow for patient-dependent attenuation maps to be measured for purposes of correcting attenuation effects in gamma camera coincidence imaging. In particularly preferred forms, the present invention is embodied in gamma-camera coincidence (GCC) imaging systems and methods which include a fixed-position point source of radiation energy.

Specifically, the preferred GCC imaging systems and methods of this invention include a pair of gamma camera imaging heads rotatable about a patient-longitudinal imaging axis. The imaging heads will each have a plurality of radiation opaque septa plates extending transversely relative to the imaging axis about which they locate. Such septa are used for emission imaging to filter out radiation originating from outside the scanner field of view. Adjacent ones of the septa plates are spaced apart along said imaging axis. At least one point source of radiation will thus be positionally fixed between a predetermined adjacent pair of the septa plates of one of the imaging heads so as to be concurrently rotatable therewith.

Further aspects and advantages of this invention will become more clear after careful consideration is given to the following detailed description of the preferred exemplary embodiments thereof.

BRIEF DESCRIPTION OF THE ACCOMPANYING DRAWINGS

Figure 4:
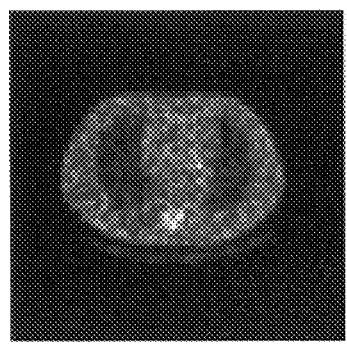
Figure 5:
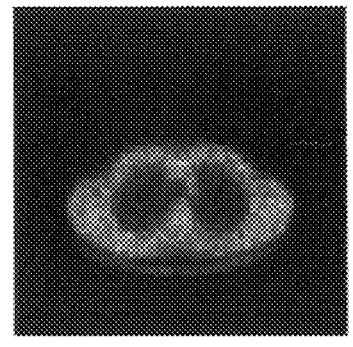

Reference will hereinafter be made to the accompanying drawing FIGURES wherein like reference numerals throughout the various FIGURES denote like structural elements, and wherein, FIG. 1 is a schematic side elevational view of a nuclear diagnostic imaging system which embodies the present invention;

FIG. 2 is a schematic cross-sectional view of the imaging system depicted in FIG. 1 as taken along line 2—2 therein; and FIGS. 3–5 are respectively cross-sectional attenuation map images of a resolution phantom, a thorax phantom and a human thorax obtained by the scanning techniques described in the Examples below.

DETAILED DESCRIPTION OF THE INVENTION

Accompanying FIGS. 1–2 schematically represent side and cross-sectional elevational views, respectively, of an imaging system 10 which embodies the principals of the present invention. In this regard, the imaging system 10 includes a pair of detector heads 12, 14 which are mounted in fixed opposed position (preferably, but not necessarily, 180° opposed) relative to one another for concurrent rotational movement about an imaging axis $A_1$ by suitable mounting on motive structures (not shown, but see the above-cited U.S. Pat. No. 5,554,848, for example). The detector heads 12, 14 are also mounted in spaced relation from one another with sufficient room therebetween for insertion of a patient table (not shown) adapted to support the weight of a patient P thereon and in substantial alignment with the imaging axis $A_1$. Preferably, the detector heads 12, 14 are mounted also for radial movements toward and away from the patient P so that the distance between the patient P and the detector heads 12, 14 may be adjustably selected.

The detector heads 12, 14 include conventional gamma cameras which include conventional scintillators and photomultiplier arrays (not shown). In addition, the detector heads 12, 14 are provided with transaxial septa 12-1, 14-1 (e.g., formed of a radiation-opaque material, such as lead, tungsten or the like) extending in planes perpendicular to the imaging axis $A_1$. In one form, the septa 12-1, 14-1 are about 3 mm thick lead or tungsten plates extending transaxially and having between about 10 to about 15 mm plate-to-plate separation distance and a depth of about 6 cm. The scintillators provide photons responsive to radiation emitting from the patient P and striking the scintillator crystal. The photons are detected and amplified by the photomultipliers to provide electrical data signals. The data signals are transferred to a control processor (not shown) which also provides command signals which command the motive means coupled to the detector heads 12, 14 to rotate in a given direction and at a given speed.

A point source 16 of a radionuclide with gamma emissions substantially higher than the 511 keV emission radiation energy is laterally fixed in position between a selected pair of transaxial septa 14-1 associated with one of the heads 14. In this regard, although the point source 16 is depicted in the disclosed embodiment as being positioned between a substantially central pair of septa 14-1 of head 14 and disposed on the gamma camera side of a diagonal plane D between the heads 12, 14 (e.g., so that all lines through the patient's body are measured at some time during a 360° acquisition), the precise positioning thereof is not critical to the functioning of the present invention. The fixed-position point source 16 thus is capable of rotating collectively with the detector heads 12, 14 in operation.

In use, the septa 12-1, 14-1 serve to collimate the radiation such that photons with a large axial (z-direction) component are unlikely to be detected keeping the data primarily two-dimensional. The point source 16 is required to be of sufficiently high energy (e.g., greater than about 511 keV) in order to be cleanly detected in the presence of the large amount of radiation being emitted from the patient's body. Preferably, Cesium-137 having radiation energy of about 660 keV has been found to be particularly useful for this purpose. In this regard, in order for the transmission scan and emission scan to match, and for patient comfort, the transmission scan is most preferably accomplished after injection of the radiopharmaceutical.

The point source 16 is most preferably included at a distal end within a rod-shaped member which may be removably inserted between a desired pair of septa 14-1a, 14-1b of the parallel septa 14-1 associated with the head 14 (i.e., so as to allow the heads 12, 14 to be operated in accordance with conventional SPECT techniques). Thus, the head 14 is most preferably provided with structures (not shown) which allow the insertion and removal of the point source 16 and which positionally fix the point source 16 relative to the head 14 when disposed between the pair of septa 14-1a, 14-1b during use.

It will be observed that regions 14-2 (see FIG. 2) of septa 14-1a, 14-1b have a greater thickness dimension as compared to other septa 14-1 associated with the head 14. This is most preferably accomplished by affixing additional lead plating to opposed surfaces of the septa 14-1a, 14-1b. In this manner, a more narrow separation distance between the septa 14-1a, 14-1b is established in the vicinity of the point source 16 thereby establishing a more narrow radiation "window" for the same.

Transmitted radiation from the point source 16 which is detected in the opposing detector head (which in the embodiment depicted is head 12) is counted in a normal single photon acquisition mode, with the heads 12, 14 rotating, either continuously or continually in a step-by-step manner, providing 360° of offset fan-beam transmission views of the object. Data may be acquired during the emission coincidence acquisition, or immediately prior to or subsequent to the emission coincidence acquisition.

Although a single point source 16 is depicted in FIGS. 1 and 2, it is possible to employ multiple point sources so as to increase the axial field of view. Furthermore, higher axial spatial resolution is achieved by increasing the thickness of the septa 14-1 in the vicinity of the point source(s) 16.

It should also be understood that while a system 10 having two heads is shown in the accompanying FIGURES, such a system represents a particularly preferred embodiment of the invention. The invention is, however, also suited in systems having other arrangements and numbers of sensing heads.

A further understanding of this invention will be obtained from the following non-limiting examples thereof.

EXAMPLES

A Varicam™ scanner commercially available from Elscint, Ltd., having coincidence imaging capability was modified to include an offset fan-beam system in accordance with the present invention. In this regard, a 0.5 mCi Cs-137 ($E_\gamma$=662 keV) point source (19.5 MBq) having a length of 13 cm, an outside diameter of about 5 mm and an active diameter of about 1 mm was inserted between a pair of septa (spacing: 1.3 cm; thickness: 3 mm; depth: 6 cm) associated with one of the gamma cameras to allow data to be acquired by the other camera in the manner shown in accompanying FIGS. 1 and 2.

The energy response of the system was sufficient so that peaks from 511 and 662 keV sources are resolved, thus allowing for the possibility of post-injection transmission scans. The intrinsic spatial resolution (FWHM of the camera was found to be slightly better at 662 keV (2.7 mm) than at 511 keV (2.9 mm). In the fan beam geometry with a single Cs-137 point source and a source-to-camera distance of 71 cm, the count rate was 7000 counts-per-second (cps).

To evaluate the noise, resolution, and general quality of images produced with this technique, several phantom and human transmission scans were performed and reconstructed using an EM algorithm. A high-count scan of the cold rod insert of a Jaszczak phantom was performed to demonstrate the capabilities of the technique. In the reconstructed low-noise attenuation map all rods (the smallest having 6.4 mm diameters and 12.7 mm separations) were resolved. (See, FIG. 3.) Attenuation maps resulting from half-hour thorax scans of phantom and human subjects were of similar quality to those typically used in PET. (See FIGS. 4 and 5, respectively.) Attenuation maps resulting from 5 minute scans may be adequate for correction of GCC data.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A gamma-camera coincidence (GCC) imaging system comprising:

a pair of gamma camera imaging heads rotatable about a patient-longitudinal imaging axis and having a plurality of radiation opaque septa plates extending transversely relative to said imaging axis and adjacent ones of said septa plates being spaced apart along said imaging axis, and a point source of radiation having a radiation energy greater than about 511 keV positionally fixedly mounted to one of said imaging heads between a selected adjacent pair of said septa plates thereof, wherein said radiation point source is disposed laterally relative to said imaging axis generally along a diagonal plane extending along said imaging axis between said pair of imaging heads so that all imaging lines through the patient's body are measured during 360° rotation of said one detector head.

2. The system of claim 1, wherein said septa are formed of lead or tungsten.

3. The system of claim 1, wherein said radiation point source is included within a rod-shaped member.

4. The system of claim 1, wherein said radiation point source is removably positioned between said adjacent pair of septa plates.

5. The system of claim 1, which includes a plurality of said radiation point sources.

6. The system of claim 1, wherein said radiation point source has a radiation energy of about 660 keV.

7. The system of claim 6, wherein said radiation point source is a cesium isotope.

8. The system of claim 7, wherein the cesium isotope is cesium-137.

9. The system of claim 1, wherein said point source is positioned between an adjacent pair of septa plates of a respective one of said gamma cameras, and wherein said adjacent pair of septa plates have a greater thickness dimension as compared to other adjacent pairs of septa plates so as to establish a lesser separation dimension therebetween.

10. A method of obtaining attenuation map images by gamma-camera coincidence imaging comprising the steps of:

(a) positionally fixing a radiation point source having a radiation energy greater than about 511 keV between an adjacent pair of plate-shaped radiation opaque septa of one gamma camera imaging head laterally of a patient-longitudinal imaging axis near a diagonal plane extending along said imaging axis between said one imaging head and an oppositely opposed another gamma camera imaging head;

(b) injecting a human or animal subject with a radiopharmaceutical;

(c) conducting a transmission scan by rotating said one gamma camera imaging head concurrently with said oppositely opposed another gamma camera imaging head about said patient-longitudinal longitudinal imaging axis so that said another gamma camera imaging head acquires transmission scan data therefrom;

(d) conducting an emission coincidence imaging scan of the subject to obtain emission scan data therefrom; and (e) combining said transmission and emission scan data to obtain attenuation-corrected cross-sectional maps of radioactivity distributions.

11. The method of claim 10, wherein steps (d) and (e) are conducted simultaneously.

12. The method of claim 10, wherein step (d) is practiced prior to step (e).

13. The method of claim 10 wherein step (d) is practiced after step (e).

14. The method of any one of claims 10–13, wherein steps (d) and (e) are practiced after step (c).

15. The method of claim 10, wherein step (c) is practiced by continuously rotating said one and another gamma cameras.

16. The method of claim 10, wherein step (c) is practiced by continually rotating in a step-by-step manner said one and another gamma cameras.

17. The method of claim 10, wherein step (a) includes removably positioning said radiation point source between said adjacent pair of septa plates.

18. The method of claim 10, wherein step (a) including positionally fixing a plurality of radiation point sources between respective adjacent pairs of septa.

19. The method of claim 10, wherein said radiation point source has a radiation energy of about 660 keV.

20. The method of claim 19, wherein said radiation point source is a cesium isotope.

21. The method of claim 20, wherein the cesium isotope is cesium-137.

22. The method of claim 10, wherein step (a) includes providing said adjacent pair of septa plates with a greater thickness dimension as compared to other adjacent pairs of septa plates so as to establish a lesser separation dimension therebetween.

* * * * *